(12) United States Patent
Dogariu et al.

(10) Patent No.: US 8,507,236 B2
(45) Date of Patent: Aug. 13, 2013

(54) SYSTEMS AND METHODS FOR CONTROLLING OBJECTS

(75) Inventors: Aristide Dogariu, Winter Springs, FL (US); Kiminobu Sugaya, Oviedo, FL (US); Gabriel Biener, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 390 days.

(21) Appl. No.: 12/791,222

(22) Filed: Jun. 1, 2010

(65) Prior Publication Data

US 2010/0301234 A1  Dec. 2, 2010

Related U.S. Application Data

(60) Provisional application No. 61/182,252, filed on May 29, 2009.

(51) Int. Cl.
*C12N 13/00* (2006.01)

(52) U.S. Cl.
USPC .................................. 435/173.1; 435/173.9

(58) Field of Classification Search
None
See application file for complete search history.

(56) References Cited

PUBLICATIONS

Wigglesworth, the Life of Insects, 1964, The New American Library, new York, pp. 200-201.*
Novikoff et al, Cells and Organelles, 1970, Holt, Rinehart and Winston, Inc. New York, pp. 12, 13, 18, and 276-280.*

* cited by examiner

*Primary Examiner* — James Martinell
(74) *Attorney, Agent, or Firm* — Thomas | Horstemeyer, LLC

(57) ABSTRACT

Systems and methods for controlling an object are disclosed. In one embodiment, a system and method pertain to irradiating the object with polarized electromagnetic radiation for a duration of time sufficient to effect a physical change with the object.

13 Claims, 5 Drawing Sheets
(3 of 5 Drawing Sheet(s) Filed in Color)

SYSTEMS AND METHODS FOR CONTROLLING OBJECTS

CROSS-REFERENCE TO RELATED APPLICATION

This application claims priority to U.S. provisional application entitled, "Systems And Methods For Regulating Cell Motility And Cell Differentiation," having Ser. No. 61/182,252, filed May 29, 2009, which is entirely incorporated herein by reference.

BACKGROUND

It is desirable in certain situation to control objects without physically contacting them. For example, it may be desirable to control the position, orientation, or configuration of living cells. Such control would be useful in a variety of clinical, diagnostic, and therapeutic uses, such as wound healing, tissue generation, and treatment and/or prevention of neurodegenerative disease and metastasis.

Various light-based methods have been proposed in the past to control dielectric objects. In one such method, the object is irradiated with highly-focused, high-intensity light so as to generate an electric field across the object having a strong intensity gradient. Once the electric field is established, the object is in effect trapped by the irradiated light and lateral movement of the apparatus that delivers the light results in corresponding lateral movement of the object. Although such a method may be used to control living cells, the high intensity of the light is undesirable given that it can damage or even kill the cells. Accordingly, it would be desirable to have an alternative mechanism for controlling a dielectric object, such as cells.

BRIEF DESCRIPTION OF THE FIGURES

The patent or application file contains at least one drawing executed in color. Copies of this patent or patent application publication with color drawing(s) will be provided by the Office upon request and payment of the necessary fee.

The present disclosure may be better understood with reference to the following figures. Matching reference numerals designate corresponding parts throughout the figures, which are not necessarily drawn to scale.

DETAILED DESCRIPTION

Introduction

Figure 1:
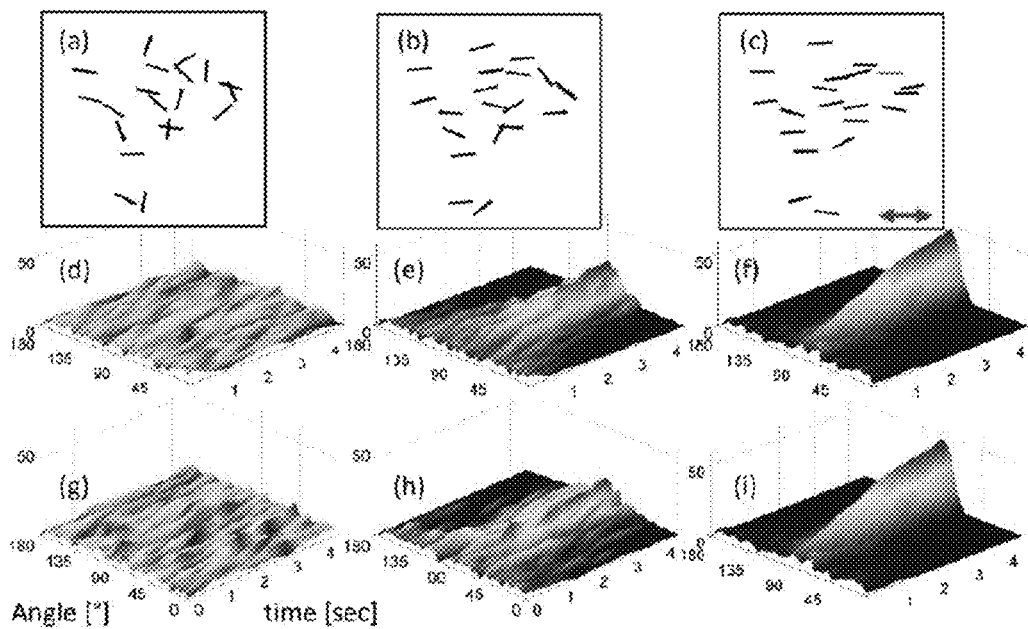
FIGS. 1(a)-1(c) illustrate the behavior of rod-like particles before and after irradiation with polarized light.
FIGS. 1(d)-1(f) illustrate the temporal evolution of the angular orientation of rod-like particles irradiated with different intensities of polarized light.
FIGS. 1(g)-1(i) illustrate the temporal evolution of the angular orientation of rod-like particles of different sizes that are irradiated with polarized light.

As described above, it is known to control dielectric objects by irradiating the object with highly-focused, high-intensity light so as to generate an electric field across the object having a strong intensity gradient. Unfortunately, such a method is an undesirable means of controlling living cells because the high intensity of the light can damage or even kill the cells. Described herein are systems and methods for controlling objects that do not require the application of high-intensity light. As is described below, objects are controlled by irradiating the objects with low-intensity polarized electromagnetic radiation, such as visible, infrared (IR), or ultraviolet (UV) light. Because the electromagnetic radiation (e.g., linearly polarized light) is of low intensity, damage to living cells is reduced or eliminated. In some embodiments, the electromagnetic radiation can be used to displace, differentiate, or divide the cells.

Cell Motility and Differentiation

The mechanisms responsible for cell reshaping and cell motility are subjects of active research. Although the molecular functions of organelles are fairly well understood, there is still no general consensus regarding the details of the mechanism that govern the overall cell behavior and determine their migration from one site to the other. Recently, it has been suggested that cell movement and reshaping may be determined by stochastic processes, such as Brownian motion or inner cell mechanical arrangements. Specifically, it has been suggested that cell motility is the result of the stochastic generation and dissolving of actin filaments.

Actin filaments (F-actin) exert forces by elongating towards the membrane of the cell. This elongation is determined by the attachment of globular actin (G-actin) monomers to the F-actin's end that is touching the membrane. The choice of G-actin attachment at one end or another is controlled by the F-actin polarity and by the critical concentrations at which G-actin monomers can attach or detach from the F-actin ends. When the plus end of an F-actin filament is the one touching the membrane and the concentration of G-actin is above the critical value, the filament will elongate towards the membrane initiating the protrusion. Under normal conditions, the displacement of G-actin is stochastic in nature and is governed by Brownian-like movement. When external forces act on either the G-actin monomers or on the F-actin filaments, their movement and, consequently, the cell growth and displacement, can be affected. This process can be controlled by applying certain external optical fields.

Controlling Cells Using External Optical Fields

The idea of mechanical action of light on matter has its origin in the corpuscular theory of light. Most of the practical applications rely on optical forces applied to particles having a refractive medium different from that of the surroundings. The applied force is, in general, dissipative as it points along the direction of propagation and results in acceleration. However, if the particle is subjected to an optical field with a significant intensity gradient, a conservative force develops which acts along the gradient of intensity. When the conservative component dominates, small particles can be trapped and controlled within the confined volume of an intense laser beam. Conservative forces also develop as a result of manipulating the wavefront or the polarization of light beams. Interestingly, apart from forces, optical fields can also exert torques and therefore can rotate small particulates. The existence of optical torques can be traced to source of mechanical action of light: the exchange of momentum between radiation and matter.

Aside from colloidal physics, light-induced forces and torques have been used in a number of biological applications. Cell plating, floating cells and chloroplast manipulation, and cell growth guiding are examples. What is common to all these applications is that trapping and manipulating cells requires fairly large optical intensities. Furthermore, because of the highly localized nature of the optical trapping field, these techniques commonly operate on single cells or on particular parts of a cell. Influencing the behavior of an entire collective of cells is a more complex problem that has not yet been approached.

It has been determined that optical torques exerted by electromagnetic fields can direct cell motility and can control the alignment of large cell clusters. As described herein, large scale guiding can be accomplished using only polarization-induced torques in the absence of any other optical forces. The cell motility is practically controlled by manipulating the stochastic motion of the G-actin monomers and F-actin filaments which, in turn, influences the directional movement of an entire cell or even the alignment and displacement of entire cluster of cells. Moreover, the manipulation of large clusters of cells is accomplished at much lower intensity levels than required for optical trapping, which opens the door for many yet to be explored applications.

The mechanism for gradual alignment of small rod-like particles subjected to both Brownian motion and polarization-induced optical torques is discussed below. This mechanism is used to explain the optical manipulation of actin filament networks. In addition, experimental results are presented below that demonstrate both the effect of light polarization on cytoskeleton and the dynamic cells guiding using optical torques.

Rod-Like Particles Subjected to Optical Torques

In the presence of an external directional field, F-actin and G-actin can be treated as dielectric rods subject to both Brownian motion and torques. This representation explains the cells' tendency to modify their motility characteristics as a result of actin filament alignment and growth in response to the applied optical field. The major elements of the model are (i) the random movement of actin filaments due to thermal forces in normal conditions, and (ii) the influence of a weak optical field through induced torques.

The G-actin monomers and the actin filaments can be regarded as rods of different dimensions. The G-actin monomers, although never measured directly, were found to be 5.5 nanometers (nm) in length and 3.5 nm in diameter using indirect measurements. The actin filaments, on the other hand, can be seen as bundle of filaments as long as 10 microns (μm) and with a diameter of 1 μm. These particles are all subject to Brownian motion due to thermal forces as well as to external forces and torques. The associated Langevin equation is $$\frac{\partial^2 x}{\partial t^2} = \Gamma^{-1}(t)\frac{\partial x}{\partial t} + \tilde{\xi}(t) + F(t) \quad (1a)$$

$$\frac{\partial^2 \theta}{\partial t^2} = \Gamma_\theta^{-1}(t)\frac{\partial \theta}{\partial t} + \tilde{\xi}_\theta(t) + T(t) \quad (1b)$$

where x and θ are the location and orientation of the particle, respectively. In Equation (1) $\tilde{\xi}(t)$ and $\tilde{\xi}_\theta(t)$ are the random processes describing the Brownian translation and rotation, Γ is the mobility tensor, and $\Gamma_\theta$ is the rotational mobility coefficient. F and T denote the external forces and torques. Assuming that the inertial effects are negligible, i.e. $\partial^2 x/\partial t^2 = \partial^2 \theta/\partial t^2 = 0$, Equation (1) can be rewritten as, $$\frac{\partial x}{\partial t} = \xi(t) + \Gamma(t)F(t), \quad (2a)$$

$$\frac{\partial \theta}{\partial t} = \xi_\theta(t) + \Gamma_\theta T(t), \quad (2b)$$

where $\xi(t)=\Gamma(t)\tilde{\xi}(t)$ and $\xi_\theta(t)=\Gamma_\theta(t)\tilde{\xi}_\theta(t)$. For simplicity, one can further consider that the random processes are Gaussian distributed with zero mean (the maximum probability to find the particle will be in its original position) and have the variance $$\langle \xi(t)\xi(t') \rangle = 2k_B T \Gamma(t)\delta(t-t') = 2D(t)\delta(t-t') \quad (3)$$

where $k_B$ is the Boltzmann's constant, T is the temperature, and D is the diffusion coefficient. The angle brackets denote an ensemble average. For rod-like particles, the diffusion coefficients are different for each degree of freedom. Of interest is a two-dimensional geometry where the diffusion coefficients corresponding to the free movement of the particle are:

$$D_a = \frac{k_B T[\ln(2r) - 0.5]}{2\pi\eta_s L}, \quad (4)$$

$$D_b = \frac{k_B T[\ln(2r) + 0.5]}{4\pi\eta_s L},$$

$$D_\theta = \frac{3k_B T[\ln(2r) - 0.5]}{\pi\eta_s L^3}$$

In Equation (4), $D_a$ and $D_b$ denote the translational diffusion coefficients along the short and the long axis of the rod-like particle, while $D_\theta$ represents the rotational diffusion coefficient. In Equation (4), $\eta_s$ is the viscosity, L and Φ are the length and diameter of the particle, and r=L/Φ. As can be seen, the rotational diffusion coefficient is strongly dependent on the particle length meaning that, for longer particles, the time in which the diffusion becomes anisotropic is longer.

Experimentation has demonstrated that macroscopic, anisotropic objects can rotate as a result of the torque exerted by a beam of circularly polarized light. Further, notable developments include the manipulation of phase and polarization distributions across the illuminating beam in order to rotate particles that are optically anisotropic. It has also been realized that the rotation of a small particle does not necessarily require an intrinsically anisotropic optical material as long as the shape is asymmetric. Linearly polarized light can exert torques on small microparticles as long as they have aspheric shapes. This can be easily explained by considering the particles as dipoles excited by the radiation's electric field. The secondary emission from these dipoles (scattering) does not necessarily need to be polarized along the direction of excitation. Hence, this modification of the direction of the electric field direction determines a torque on the particle. For anisotropic particles, this torque can be written as $$T = \int d^3x P \times E = I_0(\chi_o - \chi_e) \cdot A \cdot \Delta t \cdot \cos(2\theta) \quad (5)$$

where $P = \chi E$ is the polarizability vector of the dipole. In Equation (5), $E$ is the incident electric field, $I_0 = c\epsilon_0|E|^2$ is the beam's intensity, $\chi_o$ and $\chi_e$ are the ordinary and the extraordinary susceptibilities, $A$ is the particle cross section perpendicular to the beam propagation axis, $\Delta t$ is the measurement integration time, $\epsilon_0, c$ are the vacuum permittivity and light velocity, and $\theta$ is the angle between $P$ and $E$. As can be seen from Equation (5), the torque is maximal for an angle of 45° between the scattered and the exiting electric fields and it is minimal when they are either collinear or orthogonal. However, the orthogonal direction is a non-stable equilibrium as for smaller and larger angles the torque has opposite signs.

Consider the two-dimensional problem of rod-like actin filaments and rod-like actin monomers. For simplicity consider a plane wave illumination that is horizontally polarized (the electric field is in plane and aligned along the x axis). When using in the Langevin equation the expression for the torque in Equation (5), one obtains $$\theta = \zeta(t) + \tan^{-1}[\tan(\theta_0)e^{\alpha \Delta t}] \quad (6)$$

where $\theta_0$ is the initial alignment angle, $\alpha = \tau_0 \Gamma_\theta$, $\tau_0 = I_0(\chi_o - \chi_e) \cdot A \cdot \Delta t$, and $\zeta(t)$ is a random process with a 0 average and a variance of $2D_\theta \Delta t$.

The above-described model was used to further illustrate the behavior of rod-like Brownian particles that are subjected to optical torques of different strength. FIGS. 1(a)-1(c) show 1×10 μm rods becoming progressively aligned after an external optical torque is applied. In particular, FIG. 1(a) shows the rods before polarized light is applied, FIG. 1(b) shows the rods after polarized light has been applied for 2 seconds, and FIG. 1(c) shows the rods after polarized light has been applied for 4.5 seconds. One can see that initially, when no torque is applied, the distribution of rods' orientations are arbitrary. After applying an optical torque for 2 seconds, an increasing number of rods become aligned along the direction of polarization. Finally, after 4.5 seconds of irradiation, the majority of the rods are well aligned. Of course, the time scale of this process also depends on the level of irradiation.

FIGS. 1(d)-1(f) depict the evolution of the distribution of orientation angles for a large number of rods exposed to different levels of light intensity. Specifically, the rods in FIGS. 1(e) and 1(f) were subjected to five and ten times, respectively, more intense radiation than in FIG. 1(d). As can be seen in those figures, when increasing the intensity, the distribution function becomes narrower faster, indicating an efficient alignment of the ensemble of rods.

As shown in the preceding analysis, the magnitude of the torque depends not only on the irradiance level but also on the size of the dielectric body. This is illustrated in FIGS. 1(g)-1(i), where similar distributions of rod orientation are calculated for ensembles of rods having the same aspect ratio but different lengths, i.e., 0.2×2 μm, 0.5×5 μm, and 1×10 μm, respectively. It is clear that, in similar environmental conditions, larger rods tend to align faster for the same level of irradiation. This analysis forms the basis for explaining the experimental observations described below.

Experimental Results

Figure 2:
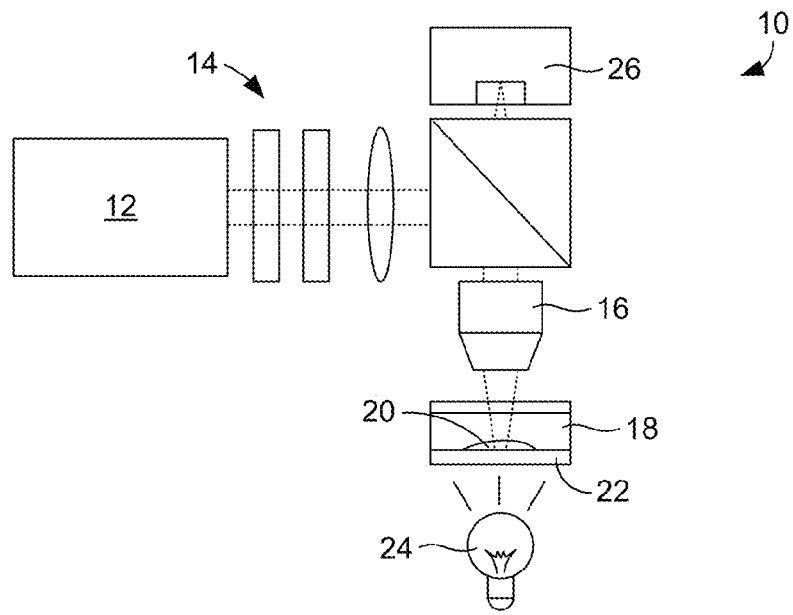
FIG. 2 illustrates an experimental setup for controlling particles using polarized light.

FIG. 2 illustrates a setup 10 that was used to investigate the effect of optical torque on cell motility. A linearly polarized doubled YAG laser beam (Intelite, model GSF32-200P, $\lambda$=532 nm, and beam intensity of P=6 mW), was generated by a laser 12 and transmitted through a polarization state generator 14 (a half-wave plate) followed by a long working distance objective lens 16 (×50 epiplan objective from Zeiss) to illuminate an incubation chamber 18 that contained cells 20 attached to a substrate 22. The cells 20 were also illuminated with unpolarized white light (power density of about 30 mW/mm$^2$) with an illumination source 24 and imaged in transmission through the same objective lens onto a charge coupled device (CCD) 26. The laser beam was filtered out using a band pass filter (now shown). The irradiation process was continued for several hours while the direction of polarization was modified every half hour. During the entire period, the cells manifested the tendency to align along the direction of polarization.

The above results were obtained using SH-SY5 neuroblastoma cells. The cells were plated at a density of 5×106 per 75 cm$^2$ in a tissue culture treated flask (Corning). The cell culture medium was Dulbecco's modified Eagle's medium with F-12 (DMEM/F12, Invitrogen) supplemented with 10% heat inactivated fetal bovine serum (Atlanta Biologics). An incubation chamber was used to maintain a humidified atmosphere of 5% $CO_2$ and 37° C. SH-SY5 cells were passed twice a week by trypsin/EDTA (Invitrogen) treatment.

In order to demonstrate the alignment of cell filaments along the direction of polarization, a fluorescence method was used in which cells, cultured and irradiated with polarized light, were fixed using ethanol and filaments were stained using phalloidin attached to a green fluorescing dye (Alexa Fluor @ 488, Invitrogen). The SH-SY5 cells were first fixed with ethanol, and then washed with phosphate-buffered saline (PBS), pH 7.4. The fixed cells were stained with the dye solution composed of 5 μl of phalloidin (Alexa Fluor @ 488, Molecular Probes) and 200 μl of PBS, followed by 20 minutes of room temperature incubation. The last stage was to wash the cover slips with PBS. The entire procedure including the incubation was conducted in the dark.

Figure 3:
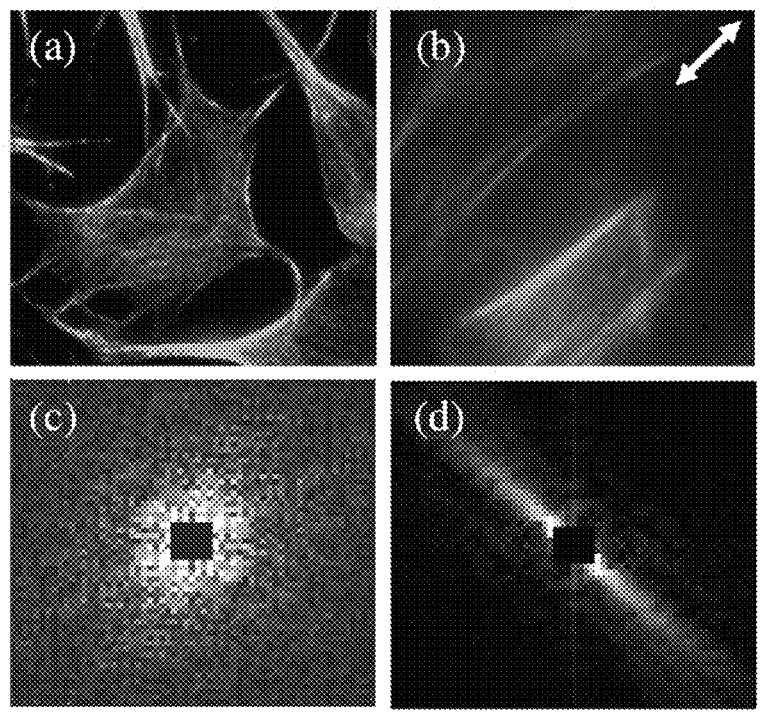
FIG. 3(a) is a fluorescence image of fixed SH-SY5 cells that have not been subjected to polarized light.
FIG. 3(b) is a fluorescence image of fixed SH-SY5 cells after being subjected to light polarized at 45°.
FIG. 3(c) is a Fourier transform distribution of the image of FIG. 3(a).
FIG. 3(d) is a Fourier transform distribution of the image of FIG. 3(b).

FIG. 3(b) depicts the fluorescent image of cells that were irradiated with polarized light along the direction indicated. For comparison, a typical fluorescence image of cells that were not irradiated with polarized light is shown in FIG. 3(a). The alignment of the actin filaments is obvious. Furthermore, a quantitative evaluation of filaments' orientations can be performed based on the Fourier analysis of the microscope images. One expects that the two-dimensional Fourier transform of an image of aligned cells or structured shapes will manifest more anisotropic features than the ones corresponding to randomly oriented cells. This is evident in FIGS. 3(c) and 3(d), in which the Fourier transforms of the corresponding images in FIGS. 3(a) and 3(b) are shown. A simple inspection of the Fourier transform images reveals the significant difference between the two examples. It is clear that in the case of polarized illumination the Fourier transform is highly asymmetric, as opposed to the situation where unpolarized illumination was used. Moreover, the asymmetry is oriented perpendicularly to the direction of polarization as a result of the filament orientation according to the results of our numerical simulations.

Figure 4:
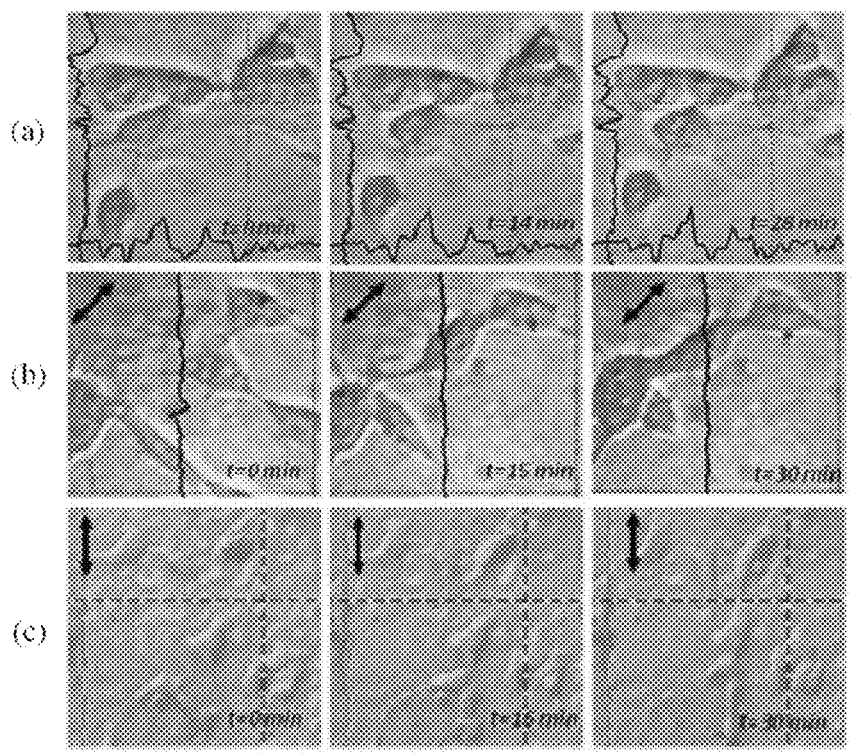
FIG. 4(a) is a time evolution of an ensemble of SH-SY5 cells exposed to unpolarized light.
FIGS. 4(b) and 4(c) are two different examples of time evolutions of SH-SY5 cells exposed to light linearly polarized along the directions indicated by the arrows.

As suggested by the simulations, the tendency of actin filaments to align along the direction of polarization can cause cell reshaping and directional movement. Even though a detailed description of such a complex dynamic process would require complex considerations, the major elements can be clearly accounted for. As a consequence of irradiation with polarized light, real-time directional movement and alignment of cells have been observed. Some of the results are illustrated in FIG. 4. Remarkably, the cells have an evident tendency to orient and move along the direction of polarization of the electric field over time in contrast to cells exposed to unpolarized light.

It is also worth noting that entire ensembles of cells gradually align along the directions of polarization indicated by the arrows. The cells tend to move along this direction, while no distinctive orientation can be observed throughout the entire examination period in the absence of polarization, as illustrated in FIG. 4(a). It is also noted that, apart from the degree of polarization, the irradiance levels are very similar for the observations illustrated in FIG. 4.

Figure 5:
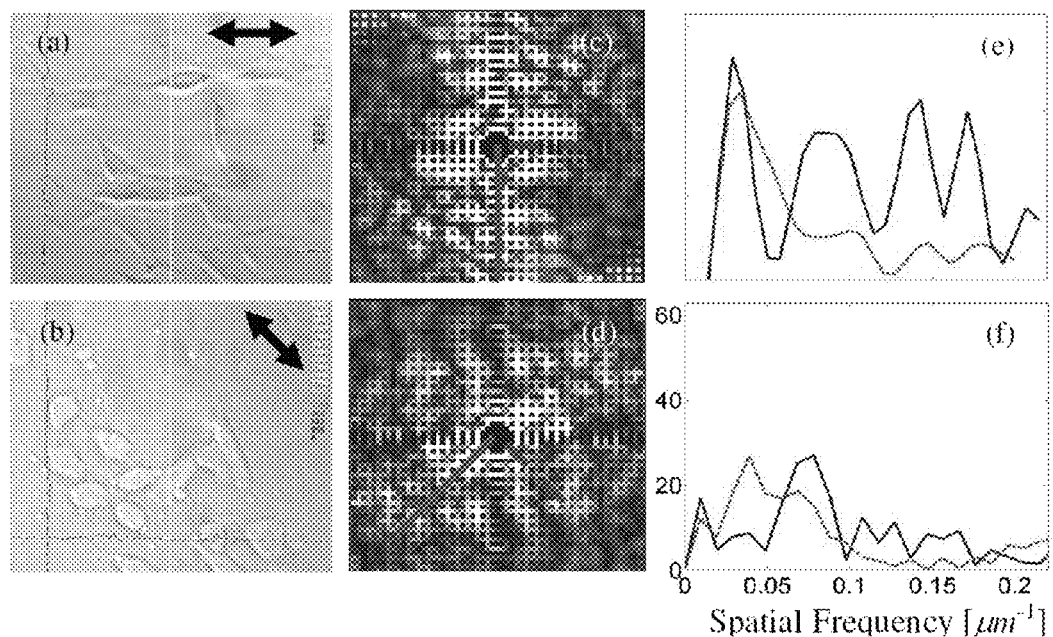
FIGS. 5(a) and 5(b) illustrate ensembles of cells illuminated with light that is linearly polarized horizontally and at 45°, respectively.
FIGS. 5(c) and 5(d) are Fourier transform distributions of the images of FIGS. 5(a) and 5(b), respectively.
FIGS. 5(e) and 5(f) are cross-sections of the Fourier transform distributions of FIGS. 5(c) and 5(d), respectively.

The cell alignment is also apparent in FIGS. 5(c) and 5(d) in which the Fourier transform along with the images of cells irradiated with light polarized horizontally and at 45° (FIGS. 5(a) and 5(b)) are shown. A simple inspection of the Fourier transforms reveals the significant difference between the two examples. It is evident in both situations that the Fourier transforms are asymmetric and, as mentioned in the preceding discussion, the asymmetries are oriented perpendicularly to the direction of polarization. To emphasize these differences even more, FIGS. 5(e) and 5(f) show two different orthogonal cross sections of the Fourier transform images. In the intermediate spatial frequency regions where the shape information resides, the different spectral content along the two orthogonal directions proves once again the anisotropy of the Fourier transforms.

It is emphasized that, in order to secure the cells' viability, all motility experiments described above were performed at low levels of light intensity (i.e., less than 40 mW/mm$^2$). The vitality of the cells was evident on images taken every 30 minutes and was also assessed by observing population growth after reincubating the cells. The absence of phototoxicity as a result of long time exposure to polarized light was also established by subjecting the cells to similar low-levels irradiation in the absence of any directional polarization. No effect on cells viability could be detected, even over extended periods of time (several hours).

Example Systems and Methods

Figure 6:
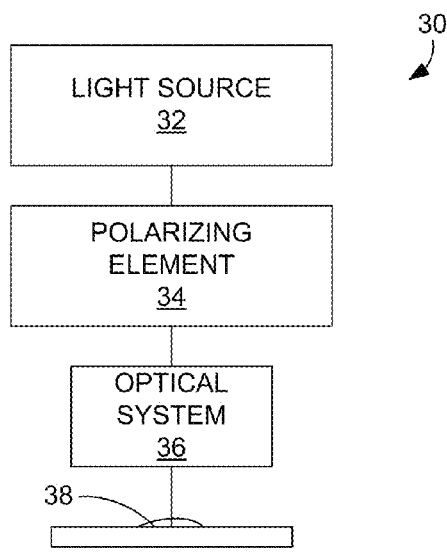
FIG. 6 is a schematic illustration of a system for controlling dielectric objects.

FIG. 6 illustrates an example system 30 that can be used to control objects, such as living cells. As indicated in FIG. 6, the system 30 includes a light (irradiation) source 32, a polarizing element 34, and an optical system 36. The light generated by the light source 32 can be coherent light (e.g., from a laser), partially-coherent (e.g., superluminescent), or incoherent (e.g., incandescent, arc, halogen, etc.) light. In some embodiments, the light generated by the light source 32 is broad-source light having a wavelength of approximately 200 to 5,000 nm and a bandwidth of approximately 1 to 500 nm. The intensity of the light can be varied temporally and, in some embodiments, can be varied spatially across the width of the beam such that different objects illuminated by the light can be irradiated by light of different intensities, if desired. In addition, the light can be turned on and off. All such adjustments can be made selectively, periodically, or randomly.

As its name suggests, the polarizing element 34 polarizes the light from the light source 32, and therefore can be used to control the polarization of the light irradiated on the objects. The polarizing element 34 can, for example, comprise one or more of a polarizer, a waveplate, an electro-optical modulator, an acoustic modulator, a liquid crystal element, and a spatial light modulator. The polarizing element 34 can polarize the light in any desired polarization direction as well as in any polarization state, such as linear, elliptical, or circular. In some embodiments, the polarizing element 34 is configured to provide different polarizations in different regions of the beam so as to enable different types of object control across the illuminated area. For example, a first direction of polarization can be provided to a first region of the light beam, and a second (different) direction of polarization can be provided to a second region of the beam. In similar manner, linear polarization can be provided in a first region of the light beam and a second (different) state of polarization (e.g., elliptical or circular) can be provided in a second region of the beam. Accordingly, objects in the first region can be controlled in a different manner than objects in the second region. Of course, more than two regions with different polarizations can be established. Such functionality can be achieved, for instance, using spatial light modulators, electro-optical modulators, microelectromechanical systems (MEMS), mirror arrays, or any type of interferometric devices. Irrespective of the device that enables such polarization control, the polarization changes can, like the light intensity changes, be made selectively, periodically, or randomly.

The optical system 36 forms a beam of polarized light that can be directed at a given target 38, such as a group of living cells. Significantly, the optical system 36 does not tightly focus the polarized light. To the contrary, the optical system 36 emits a substantially unfocused, broad field of light (i.e., large plain wave) that is, for example, hundreds of microns across. In this manner, the cells are not subjected to high intensity light and a large number (e.g., group) of cells can be affected at the same time, if desired. In some embodiments, the light irradiated on the cells has an intensity of less than approximately 100 W/m$^2$. The optical system 36 can comprise one or more of an objective, a lens, a telescope, reflective optics, and refractive optics.

Figure 7:
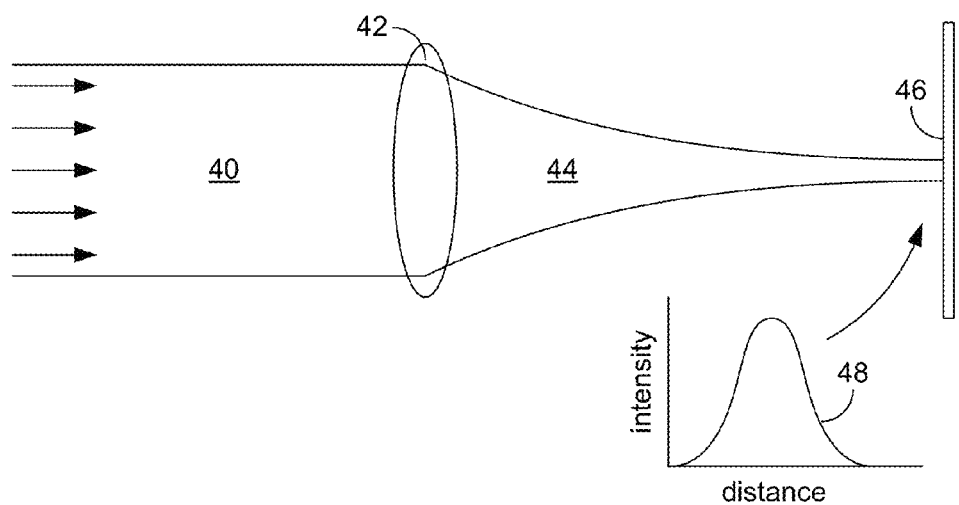
FIG. 7 is a schematic depiction of irradiating an object with focused, high-intensity light.
Figure 8:
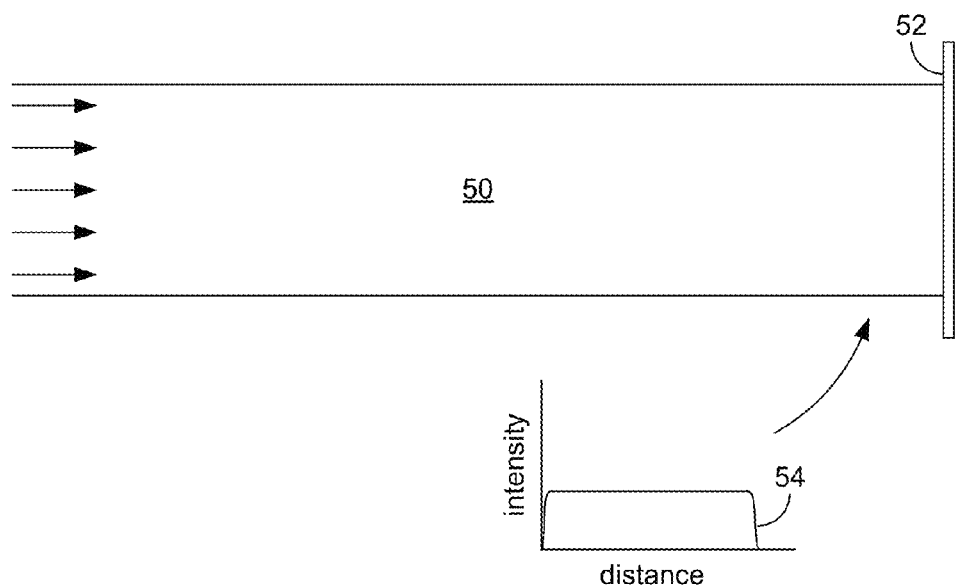
FIG. 8 is a schematic depiction of irradiating an object with unfocused, low-intensity light.

As noted above, substantially unfocused polarized light is used to reduce the intensity of the light that is irradiated upon the objects to be controlled. By using unfocused light, the light beam applied to the object has substantially no intensity gradient. This is depicted in FIGS. 7 and 8. In FIG. 7, a beam of light 40 is focused by a focusing lens 42 to produce a focused beam 44 that is irradiated on a target 46, such as a slide that supports living cells. Because the beam is focused, it has a high intensity gradient, as indicated by the curve 48. In contrast, FIG. 8 shows a beam of light 50 that is not focused, resulting in an unfocused beam that is irradiated on a target 52. Because the beam is unfocused, it has a little or no intensity gradient, as indicated by the curve 54.

Figure 9:
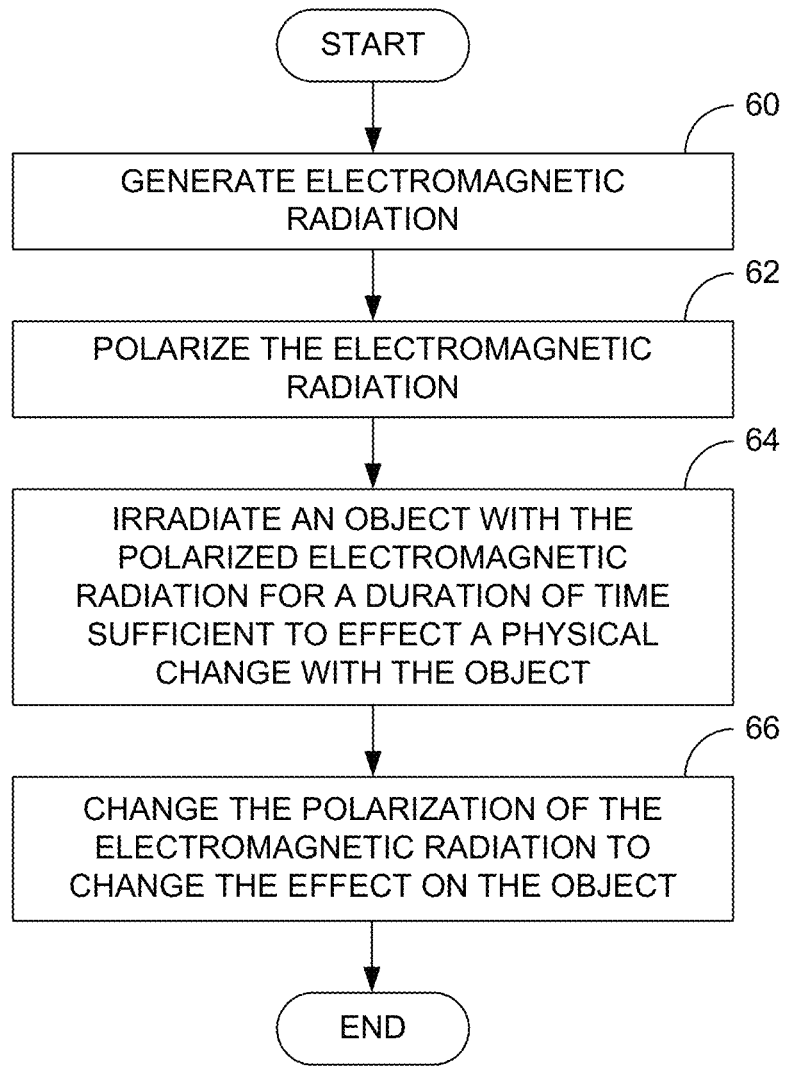
FIG. 9 is a flow diagram of an example method for controlling an object.

FIG. 9 illustrates an example method for controlling an object. Beginning with block 60, electromagnetic radiation is generated. As described above, the electromagnetic radiation can comprise light, such as coherent light, partially-coherent, or incoherent light. In some embodiments, the light is an unfocused, broad field of polarized light having substantially no intensity gradient. The light further can be low-intensity light having an intensity less than approximately 100 W/m$^2$.

With reference to block 62, the electromagnetic radiation is polarized. As mentioned above, the polarization can be linear polarization of a desired polarization direction, or another state of polarization, such as elliptical or circular polarization. In addition, the light can have different polarization (direction and/or state) in different regions of the electromagnetic radiation.

Referring next to block 64, an object is irradiated with the polarized electromagnetic radiation for a duration of time sufficient to effect a physical change with the object. In cases in which linearly polarized light is used, the light applies an optical torque to the object irradiated by that light that tends to align the object with a direction of polarization of the light.

Therefore, the physical change can comprise longitudinal alignment of the object along the direction of polarization. In embodiments in which the object is a cell, the physical change can comprise alignment of filaments of the cell along the polarization direction and, ultimately, alignment of the cell along the direction of polarization. If the cell is aligned along the polarization direction for a sufficient duration of time, the cell can ultimately move along the direction of polarization and/or divide along the direction of polarization. When there are multiple objects (e.g., cells) within the irradiated electromagnetic radiation, multiple objects (e.g., cells) can be simultaneously subjected to a physical change, such as alignment, movement, or division along the direction of polarization. It is further noted that the physical effect on the cell can comprise the immobilization of the cell, for instance when the polarization is elliptical or circular.

Referring next to block 66, the polarized electromagnetic radiation is changed to change the effect on the object. As expressed above, such a change can comprise changing the intensity of the light and/or changing the polarization of the light, temporally and/or spatially (e.g., according by region). In terms of polarization, the change can be a change in the direction of polarization, or a change in the state of polarization. Therefore, the behavior (e.g., movement) of the object can be controlled as desired.

Novel means for directing and controlling cells motility have been described herein. The disclosed mechanisms for guiding cell motility exploits the optical torque exerted on the actin filaments that are part of the cytoskeleton which, in turn, is responsible for the cell movement and cell reshaping. A physical model has been presented explaining this phenomenon by assuming that the G-actin monomers and the F-actin filaments act as anisotropic dipoles characterized by a certain orientation of their polarizability vectors. Consequently, when a polarized field is applied, the optical torque exerted on the filaments biases their Brownian motion, which eventually leads to directional movement and reshaping of the cells. The experimental observations are well described by a simple model considering rod-like actin filament that is simultaneously subjected to Brownian motion and a directional external field.

It is reiterated that the disclosed results were achieved with low intensity illumination such that the cells' viability was secured. The non-invasiveness of the disclosed procedures was clearly confirmed by the images taken for several hours at 30 minutes intervals. The experiments also included non-polarized illumination with similar intensity levels which also demonstrate the absence of photo-toxicity. In addition, the cells viability was also examined by observing population growth after reincubating the exposed cells.

Finally, apart from cells directional motility, the tendency of large groups of cells to preferentially align when exposed to linearly polarization radiation was experimentally demonstrated.

Although two-dimensional cell manipulation has been discussed in the foregoing disclosure, other forms of manipulation can be performed. For example, cells can be displaced in three dimensions in cases in which the cell is suspended in a three-dimensional (3D) space. Such displacement can be achieved, for instance, by using multiple discrete polarized light sources, each of which acts upon the cell. Furthermore, instead of displacing a cell, the cell could instead be rotated in place. Such rotation can be effected by, for example, rotating the light source to obtain similar rotation of the cell or collection of cells. In addition, cell manipulation can include cell deformation without actual displacement of the cell.

It is further noted that multiple cells can be displaced at the same time in different directions, for example to bring the cells next to each other. Such control is useful in accessing cell interaction at a fundamental level and may aid in understanding how certain drugs affect communication between cells. In some embodiments, different cells can be brought together by applying different polarizations to the cells using a single source or multiple sources. It is also noted that the broad field of polarized light can be left constant in time, or can be pulsed or slowly varied in intensity and/or polarization over time. Moreover, the polarization can be constant across the field or varied.

The invention claimed is:

1. A method for controlling a living cell, the method comprising:
    irradiating the cell with a broad field of polarized light having substantially no intensity gradient to apply an optical torque on the cell, the polarized light having a selected direction of polarization; and
    maintaining the irradiation of the cell with the polarized light for a duration of time sufficient to cause filaments of the cell to align with the direction of polarization.

2. The method of claim 1, further comprising changing an intensity of the polarized light.

3. The method of claim 1, further comprising changing a state of polarization of the polarized light.

4. The method of claim 1, further comprising changing the polarized light temporally.

5. The method of claim 1, further comprising changing the polarized light spatially.

6. The method of claim 1, further comprising maintaining the irradiation of the cell for a period of time sufficient to cause the cell to move along the polarization direction.

7. The method of claim 1, further comprising maintaining the irradiation of the cell for a period of time sufficient to cause the cell divide along the polarization direction.

8. The method of claim 1, wherein irradiating the cell comprises irradiating the cell with light having an intensity less than approximately 100 W/m$^2$.

9. The method of claim 1, wherein irradiating the cell comprises simultaneously irradiating a group of cells with the broad field of polarized light to cause filaments of multiple cells of the group to align with the direction of polarization.

10. The method of claim 1, further comprising changing the polarization direction of the polarized light to change the alignment of the filaments of the cell.

11. The method of claim 1, wherein irradiating the cell with a broad field of polarized light comprises irradiating the cell with a broad field of linearly polarized light.

12. The method of claim 1, wherein irradiating the cell with a broad field of polarized light comprises irradiating the cell with a broad field of circularly polarized light.

13. The method of claim 1, wherein irradiating the cell with a broad field of polarized light comprises irradiating the cell with a broad field of elliptically polarized light.

* * * * *